United States Patent
Ding et al.

(10) Patent No.: US 7,335,382 B1
(45) Date of Patent: Feb. 26, 2008

(54) COMPOSITIONS AND METHODS FOR THE TREATMENT AND PREVENTION OF CANCER

(75) Inventors: Xian-Zhong Ding, Wilmette, IL (US); Thomas E. Adrian, Chicago, IL (US); Peter D. Collin, Sunset, ME (US)

(73) Assignee: Northwestern University, Evanston, IL (US)

( * ) Notice: Subject to any disclaimer, the term of this patent is extended or adjusted under 35 U.S.C. 154(b) by 283 days.

(21) Appl. No.: 11/066,802

(22) Filed: Feb. 25, 2005

Related U.S. Application Data (60) Provisional application No. 60/547,527, filed on Feb. 25, 2004.

(51) Int. Cl.
*A61K 35/36* (2006.01)
*A61K 35/12* (2006.01)

(52) U.S. Cl. ...................... 424/574; 424/520

(58) Field of Classification Search ............ None
See application file for complete search history.

(56) References Cited

U.S. PATENT DOCUMENTS

| | | | | |
|---|---|---|---|---|
| 5,770,205 A | * | 6/1998 | Collin | 424/520 |
| 5,876,762 A | * | 3/1999 | Collin | 424/520 |
| 5,985,330 A | * | 11/1999 | Collin | 424/520 |
| 6,399,105 B1 | * | 6/2002 | Collin | 424/550 |
| 6,767,890 B1 | * | 7/2004 | Collin | 514/2 |
| 2004/0266999 A1 | * | 12/2004 | Kuriki et al. | 536/8 |

OTHER PUBLICATIONS

Szulgit et al. J. Exp. Biol. 2000. vol. 203, pp. 1539-1550.*
Trotter et al. Comp. Biochem. Physiol. 1997. vol. 116A, No. 4, pp. 329-335, AQUASCI Abstract enclosed.*

* cited by examiner

*Primary Examiner*—Christopher R. Tate
(74) *Attorney, Agent, or Firm*—Casimir Jones, S.C.

(57) ABSTRACT

The present invention relates to new classes of anti-cancer agents. In particular, the present invention provides materials derived from natural sources as anti-cancer agents, alone, or in combination with other anti-cancer agents or therapies.

12 Claims, 3 Drawing Sheets

FIGURE 1

Effect of Test Substances on Prostate, PC-3 Tumor Cell

| Treatment | Assay Name | Percent Growth (Mean ± SEM, n = 2) | | | | | | | |
|---|---|---|---|---|---|---|---|---|---|
| | | Blank | Time$_0$ | Vehicle | Concentration (%) | | | | |
| | | | | | 0.1 | 0.01 | 0.001 | 0.0001 | 0.00001 |
| PT# 1036100 (CBR-12) (CBR-A56634CM) | 371900, Prostate, PC-3 | -100 | 0 | 100 | -97±1 | -82±3 | 22±10 | 88±5 | 93±3 |
| PT# 1036101 (CBR-13) (CBR-A56634CMNS) | 371900, Prostate, PC-3 | -100 | 0 | 100 | -95±1 | -88±3 | 96±3 | 94±1 | 94±5 |
| | | | | | Concentration (µM) | | | | |
| | | | | | 10 | 1 | 0.1 | 0.01 | 0.001 |
| Mitomycin | 371900, Prostate, PC-3 | -100 | 0 | 100 | -46±9 | 21±6 | 50±1 | 77±2 | 95±1 |

FIGURE 2

The Summary of IC$_{50}$, TGI and LC$_{50}$ Values

| Treatment | Assay # | Assay Name | $^a$IC$_{50}$ | $^b$TGI | $^c$LC$_{50}$ |
|---|---|---|---|---|---|
| PT# 1036100 (CBR-12) (CBR-A56634CM) | 371900 | Tumor, Prostate, PC-3 | 0.00055% | 0.0014% | 0.0038% |
| PT# 1036101 (CBR-13) (CBR-A56634CMNS) | 371900 | Tumor, Prostate, PC-3 | 0.0026% | 0.0038% | 0.0056% |
| Mitomycin | 371900 | Tumor, Prostate, PC-3 | 0.14 µM | 1.6 µM | >10 µM |

$^a$IC$_{50}$ (50% Inhibition Concentration): Test compound concentration where the increase from time$_0$ in the number or mass of treated cells was only 50% as much as the corresponding increase in the vehicle-control at the end of experiment.
$^b$TGI (Total Growth Inhibition): Test compound concentration where the number or mass of treated cells at the end of experiment was equal to that at time$_0$.
$^c$LC$_{50}$ (50% Lethal Concentration): Test compound concentration where the number or mass of treated cells at the end of experiment was half that at time$_0$.

A semi-quantitative determination of IC$_{50}$, TGI and LC$_{50}$ was carried out by nonlinear regression analysis using GraphPad Prism (GraphPad Software, USA).

FIGURE 3

The concentration-response curves for growth inhibition in PC-3 tumor cell treated with test substances

COMPOSITIONS AND METHODS FOR THE TREATMENT AND PREVENTION OF CANCER

The present invention claims priority to U.S. Provisional Patent Application Ser. No. 60/547,527, filed Feb. 25, 2004, the disclosure of which is herein incorporated by reference in its entirety.

The present invention was made in part under the National Cancer Institute of USA Grant No. CA72717. The government may have certain rights in the invention.

FIELD OF THE INVENTION

The present invention relates to new classes of anti-cancer agents. In particular, the present invention provides materials derived from natural sources as anti-cancer agents, alone, or in combination with other anti-cancer agents or therapies. These anticancer materials find use in therapeutic, research, and drug screening applications.

BACKGROUND

While new cancer therapies are continuously being discovered, there remains a great need for new anti-cancer compounds and therapies, particularly for cancers such as pancreatic cancer, which is largely untreatable with current therapies.

DEFINITIONS

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "initial diagnosis" refers to a test result of initial cancer diagnosis that reveals the presence or absence of cancerous cells (e.g., using a biopsy and histology).

As used herein, the term "post surgical tumor tissue" refers to cancerous tissue that has been removed from a subject (e.g., during surgery).

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

As used herein, the terms "anticancer agent," "conventional anticancer agent," or "cancer therapeutic drug" refer to any therapeutic agents (e.g., chemotherapeutic compounds and/or molecular therapeutic compounds), radiation therapies, or surgical interventions, used in the treatment of cancer (e.g., in mammals).

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

The term "derivative" of a compound, as used herein, refers to a chemically modified compound wherein the chemical modification takes place either at a functional group of the compound, aromatic ring, or carbon backbone. Such derivatives include esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

An "effective amount" is an amount sufficient to effect beneficial or desired results. An effective amount can be administered in one or more administrations.

As used herein, the term "administration" refers to the act of giving a drug, prodrug, or other agent, or therapeutic treatment (e.g., radiation therapy) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Coadministration" refers to administration of more than one chemical agent or therapeutic treatment to a physiological system (e.g., a subject or in vivo, in vitro, or ex vivo cells, tissues, and organs). "Coadministration" of the respective chemical agents and therapeutic treatments may be concurrent, or in any temporal order or physical combination.

DETAILED DESCRIPTION OF THE INVENTION

The present invention relates to new classes of anti-cancer agents. In particular, the present invention provides materials derived from natural sources as anti-cancer agents, alone, or in combination with other anti-cancer agents or therapies.

For example, the present invention provides multi-solvent extracts derived from *C. frondosa* epithelial skin powder (see e.g., U.S. Pat. No. 5,770,205, herein incorporated by reference in its entirety, for preparation of fractions of sea cucumbers), components thereof, and related compositions for use in the treatment of cancer, including pancreatic cancer.

In some embodiments, it is shown that the extract A5 has anti-tumor activity. Experiments describing these results are provided in Dong et al., World J. Gastroenterol., 10:105 (2004), herein incorporated by reference in its entirety. A5 has shown inhibition of the prostaglandin receptor EP-1, PGE2, COX 1 and 2 and 5-lipoxygenase related activity. A5 markedly inhibited pancreatic cancer cell proliferation and induced apoptosis in pancreatic cancer cells. Cytochrome C release was observed in the A5-mediated apoptosis in pancreatic cancer cells, suggesting that the mitochondrial pathway is involved, although an understanding of the mechanism is not necessary to practice the present invention and the present is not limited to any particular mechanism of action. Example 1, below provides an extraction protocol for preparing A5.

Using TLC, HPLC, GC and NMR, it was established that A5 and its derivatives is composed of the following ingredients: sterols, fatty acids, glycosides, and phospholipids composed principally of alkenylacylGPE, (phosphotidylethanolamine) and AlkylacylGPC, (phosphotidylcholine). Phospholipids account for approximately 19% of the A5 compound. Principal fatty acids within A5-CM include EPA, 12-methyltetradecanoic acid, and palmitoleic acid.

The A5 product has been shown to include the following activities:

In vitro: Significant inhibition of pancreatic and prostate cancer cell proliferation as evidenced by inhibition of labeled thyrnidine incorporation, induction of apoptosis (programmed cell death), inhibition of eicosanoid pathways, including 5-lipoxygenase, COX-1 and COX-2, and antagonism of the prostanoid receptor EP-1.

In vivo: A5 has shown in vivo anti-proliferative activity in orthotopically transplanted tumors in immune competent hamsters.

In some embodiments, the present invention provides A5-CM, a multi-solvent extract of dried *C. frondosa* epithelial skin powder. Dried skins are prepared and extracted using isopropanol/water in a 66:34 ratio, followed by chloroform/methanol (2:1) to produce A5-CM, a viscous dark oil. *Cucumaria frondosa*, collected and pooled from September, January, March, 2000 near Stonington, Me. was used. The precipitate from the chloroform/methanol extraction, A5-P also may be used as an anti-cancer material. Glycosyl composition analysis of the A5-P precipitate revealed the presence of ribose, fucose, xylose, a deoxyhexose, methylated hexose, gal actose, glucose, mannose and N-acetyl glucosamine, although the present invention is not limited to materials having these components.

HPLC quality control fingerprints show relationships between HPLC spectra of fatty acids, sterols and phospholipids. Conducting these quality parameter protocols allows confirmation of reproducibility of manufacturing which is correlated with excellent biological reproducibility of the preparations as well.

A5-CM alters several chemopreventive and treatment targets known to be involved in cancer processes. These include:

1. 5-lipoxygenase
2. COX-1 and 2
3. epoxidation of estrogen 4. caspases, BCL, PPAR gamma 5. labeled thymidine incorporation Additional extracts with anti-tumor activity are described in Example 2, below.

Pharmaceutical Compositions

The present invention further provides pharmaceutical compositions (e.g., comprising the materials described above. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compositions of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24, 25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether.

In some embodiments, drug delivery systems are used that deliver the pharmaceutical compositions of the present invention directly to the gut. Several types of colonic drug delivery systems are currently available, including enemas (Sutherland et al., Med. Clin. North Amer., 74, 119 (1990)); rectal foams (Drug. Ther. Bull., 29, 66 (1991)); and delayed release oral formulations in the form of Eudragit-coated capsules which dissolve at pH 7 in the terminal ileum (Schroeder et al., New Engl. J. Med., 317, 1625 (1987)). In other embodiments enteric coatings, which remain undissociated in the low pH environment of the stomach, but readily ionize when the pH rises to about 4 or 5 are utilized, including, but not limited to, polyacids having a pH of 3 to 5.

Dosing is dependent on severity and responsiveness of the disease state to be treated. Optimal dosing schedules can be calculated from measurements of drug accumulation in the body of the patient. The administering physician can readily determine optimum dosages, dosing methodologies and repetition rates. Optimum dosages may vary depending on the relative potency of individual compositions of the present invention, and the delivery means, and can generally be estimated based on $EC_{50}$s found to be effective in in vitro and in vivo animal models or based on the examples described herein. In general, dosage is from 0.01 μg to 10 mg per kg of body weight (although the present invention is not limited to this range), and may be given once or more daily, weekly, monthly or yearly. In some embodiments, dosage is continuous (e.g., intravenously) for a period of from several hours to several days or weeks. In some embodiments, treatment is given continuously for a defined period followed by a treatment free period. In some embodiments, the pattern of continuous dosing followed by a treatment free period is repeated several times (e.g., until the disease state is diminished).

The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the composition is administered in maintenance doses.

Combination Therapy

In some embodiments, the materials of the present invention are provided in combination with existing therapies. In some embodiments, the materials of the present invention are provided in combination with known cancer chemotherapy agents. The present invention is not limited to a particular chemotherapy agent.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. The below Table provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |

-continued

| | | |
|---|---|---|
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a, a, a', a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |

-continued

| | | |
|---|---|---|
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicm liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3, 17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2', 2-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro Azgly-NH2 acetate [$C_{59}H_{84}N_{18}O_{14}$•$(C_2H_4O_2)_x$ | Zoladex Implant | AstraZeneca Pharmaceuticals |

-continued

| | | |
|---|---|---|
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3', 4': 6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl)amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, PA |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |

| | | |
|---|---|---|
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a,4,7β,10β,13a-hexahydroxytax-11-en-9-one 4,10-diacetate 2-benzoate 13-ester with (2R, 3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methythydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}$ $(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as tetrazine-8-carboxamide) | Temodar | Schering |
| Teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H, 12H)-dione monohydrochloride) | Hycamtin | GlaxoSmithKline |

-continued

| | | |
|---|---|---|
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG$_{2a}$ lambda anti-CD20 antibody (I 131 is a radioimmunotherapeutic antibody)) | Bexxar | Corixa Corp., Seattle, WA |
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

EXAMPLES

The following examples are provided in order to demonstrate and further illustrate certain preferred embodiments and aspects of the present invention and are not to be construed as limiting the scope thereof.

Example 1

Preparation of Agents

Live sea cucumbers—*Cucumaria frondosa*

Extraction of guts and meat tissues

Heating in water for 10 minutes at 80 C.

Cooling and separating epithelial layer from endoderm

Saving of the epithelial layer

Drying at low heat for two days

Powdering in hammer mill at room temperature

Extraction of epithelial layer with isopropanol/water (66:34)

Extraction Protocols:

Twenty grams of dry sea cucumber epithelial layer tissue powder are placed in a 1-liter vessel with lid. Eighty mL of water is mixed with 120 mL of isopropanol and stirred at room temperature, and then added to powder and stirred and left to stand for approximately 12 hours. Other proportions of water/isopropanol or water/alcohols can suffice, but preferably, a 66:34 isopropanol/water proportion is suitable for this invention.

The extract is then decanted and put through a Buchner funnel with a Whatman #2 filter disc under vacuum. The filtered extract is then roto-vaped to dryness.

Example 2

Testing of Agents

Additional extracts with were shown to have anti-tumor activity. In particular, two A5-CM precipitates were generated and tested. Starting with A5, produced by the methods described above, chloroform/methanol 2:1 is added to the A5 in a proportion between 5:1 solvent to A5 and 20:1 solvent to A5. A light colored precipitate is formed and separated by any standard method known in the art. The precipitate so formed is a light powder. CBR-A56634CM is the above material, without the precipitate. CBR-A56634CM was shown to have anti-cancer activity in prostate cancer cells as shown below. A second extract, CBR-A56634CMNS is the CBR-A56634CM described above, prepared with an additional saponification step. By "NS", the extract refers to the non-saponifiable portion, which shows anti-5-lipoxygenase activity.

The assay used to detect changes in cell proliferation is based on the ability of viable cells to cause alamarBlue to change from its oxidized (non-fluorescent, blue) to a reduced (fluorescent, red) form. With the results obtained from the alamarBlue reaction, cell proliferation can be quantified and metabolic activity of viable cells examined. Test compounds, were tested for possible effect on the proliferation of human prostate tumor cell line-PC-3, at five final assay concentrations of 0.1%, 0.01%, 0.001%, 0.0001% and 0.00001% through serial 10-fold dilutions. The agents caused significant growth inhibition (less than or equal to 50% of growth) at concentrations between 0.0001% or 0.001% and 0.1% relative to a vehicle treated control in PC-3 tumor cell line. Significant activity was observed for the concurrently tested standard reference agent Mitomycin at <10 mM. Consequently, a semi-quantitative determination of estimated IC$_{50}$ (50% inhibition concentration), TGI (total growth inhibition) and $LC_{50}$ (50% lethal concentration) by nonlinear regression analysis was calculated.

1. Test Substance and Concentration

The test compounds were dissolved in 100% DMSO and immersed in ultrasonic cleaner for 15 minutes, then diluted with distilled water to obtain initial working solutions of 10%, 1%, 0.1%, 0.01% and 0.001% in 40% DMSO. A 100-fold dilution was further made in the culture media to generate final assay concentrations of 0.1%, 0.01%, 0.001%, 0.0001% and 0.00001% in 0.4% DMSO.

2. Cell Culture Media

The tumor cell line PC-3 (human prostate adenocarcinoma), obtained from American Type Culture Collection (ATCC CRL-1435), was incubated in air atmosphere of 5% $CO_2$ at 37° C. The culture medium used was F-12K Nutrient Mixture (Kaighn's Modification) with 3% fetal bovine serum, which was supplemented with 1% Antibiotic-Antimycotic.

3. Chemicals

AlamarBlue (Biosource, USA), Antibiotic-Antimycotic (GIBCO BRL, USA), F-12K Nutrient Mixture (Kaighn's Modification) (GIBCO BRL, USA), Fetal Bovine Serum (HyClone, USA), Mitomycin (Kyowa, Japan).

4. Equipment $CO_2$ Incubator (Form a Scientific Inc., USA), Centrifuge 5810R (Eppendorf, Germany), Hemacytometer (Hausser Scientific Horsham, USA), Inverted Microscope CK-40 (Olympus, Japan), System Microscope E-400 (Nikon, Japan), Spectrafluor Plus (Tecan, Austria), Ultrasonic cleaner (Branson, USA) and Vertical Laminar Flow (Tsao Hsin, R. O. C.).

1. Evaluation of Anti-Proliferation for Test Substances

Aliquots of 100 µl of cell suspension (about $2.5 \times 10_3$/well) were placed in 96-well microtiter plates in an atmosphere of 5% $CO_2$ at 37° C. After 24 hours, 100 µl of growth medium and 2 µl of test solution, mitomycin or vehicle (40% DMSO), were added respectively per well in duplicate for an additional 72-hour incubation. Thus, the final concentration of DMSO was 0.4% and the test compounds were evaluated at concentrations of 0.1%, 0.01%, 0.001%, 0.0001% and 0.00001%. At the end of incubation, 20 µl of 90% alamarBlue reagent was added to each well for another 6-hour incubation before detection of cell viability by fluorescent intensity. Fluorescent intensity was measured using a Spectrafluor Plus plate reader with excitation at 530 nm and emission at 590 nm.

2. Determination of $IC_{50}$, TGI and $LC_{50}$

The measured results was calculated by the following formula:

$PG(\%) = 100 \times (\text{Mean } F_{test} - \text{Mean } F_{time0})/(\text{Mean } F_{ctrl} - \text{Mean } F_{time0})$ If $(\text{Mean } F_{test} - \text{Mean } F_{time0}) < 0$, then $PG(\%) = 100 \times (\text{Mean } F_{test} - \text{Mean } F_{time0})/(\text{Mean } F_{time0} - \text{Mean } F_{blank})$ Where:

PG: percent growth

Mean $F_{time0}$=The average of 2 measured fluorescent intensities of reduced alamarBlue at the time just before exposure of cells to the test substance.

Mean $F_{test}$=The average of 2 measured fluorescent intensities of alamarBlue after 72-hour exposure of cells to the test substance.

Mean $F_{ctrl}$=The average of 2 measured fluorescent intensities of alamarBlue after 72-hour incubation without the test substance.

Mean $F_{blank}$=The average of 2 measured fluorescent intensities of alamarBlue in medium without cells after 72-hour incubation.

A decrease of 50% or more (>50%) in fluorescent intensity relative to vehicle-treated control indicated significant cell growth inhibition, cytostatic or cytotoxic activity, and a semi-quantitative $IC_{50}$, TGI and $LC_{50}$ were then determined by nonlinear regression using GraphPad Prism (GraphPad Software, USA).

$IC_{50}$ (50% Inhibition Concentration): Test compound concentration where the increase from $time_0$ in the number or mass of treated cells was only 50% as much as the corresponding increase in the vehicle control at the end of experiment.

TGI (Total Growth Inhibition): Test compound concentration where the number or mass of treated cells at the end of experiment was equal to that at time 0.

$LC_{50}$ (50% Lethal Concentration): Test compound concentration where the number or mass of treated cells at the end of experiment was half that at time 0.

Figure 1:
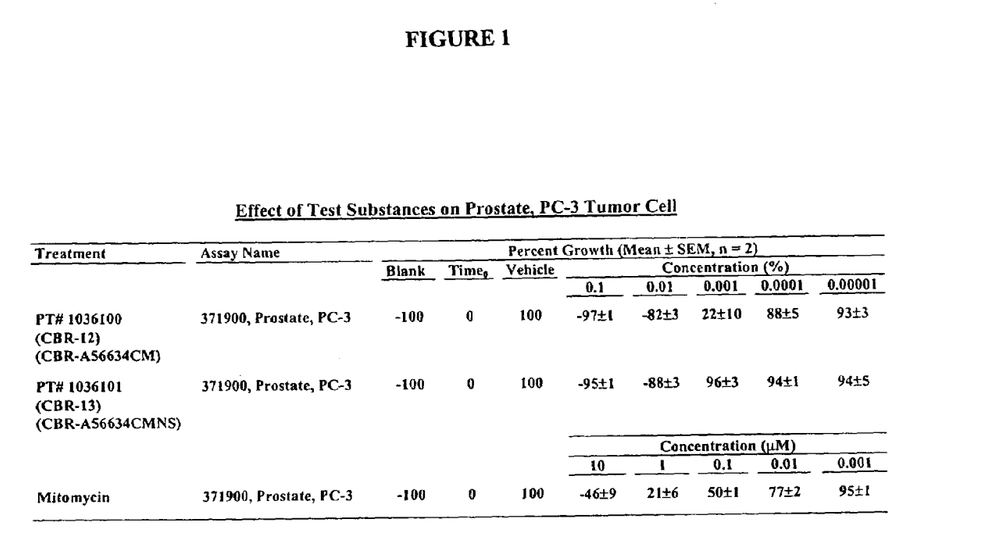
FIG. 1 provides a table showing the effect of test substrates on PC-3 prostate tumor cell growth.
Figure 2:
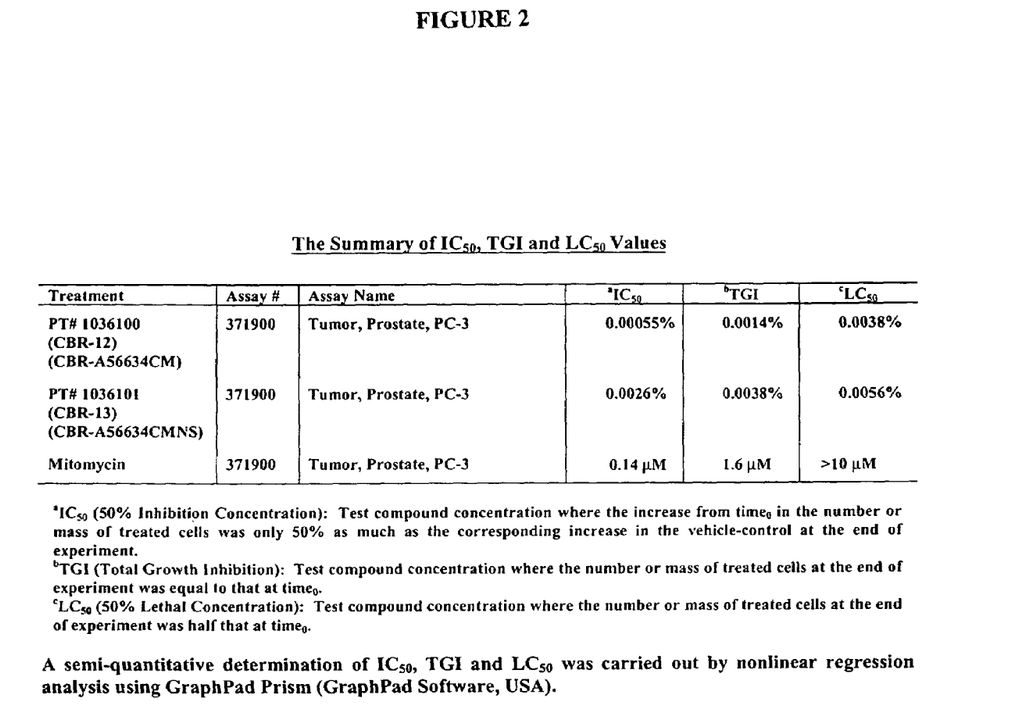
FIG. 2 provides a table showing the inhibition concentrations, total growth inhibition, and lethal concentrations of materials in some embodiments of the present invention.
Figure 3:
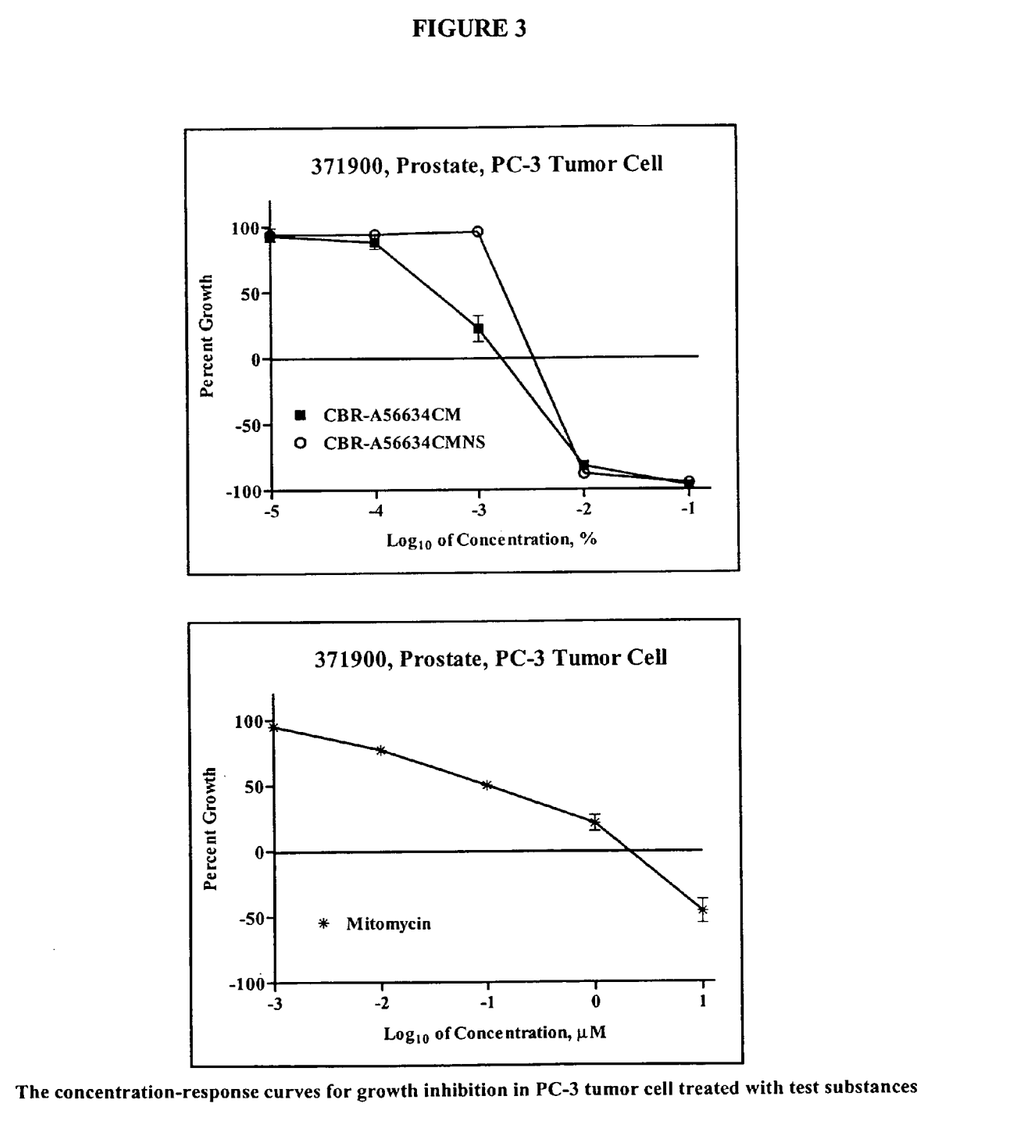
FIG. 3 provides graphs showing growth of PC-3 prostate tumor cells versus concentration of materials in some embodiments of the present invention.

CBR-A56634CM and CBR-A56634CMNS caused significant growth inhibition (<50% of growth) at concentrations between 0.0001% or 0.001% and 0.1% relative to a vehicle treated control in PC-3 tumor cell line. Significant activity was observed for the concurrently tested standard reference agent Mitomycin at <10 µM (FIGS. 1 and 3). Consequently, a semi-quantitative determination of estimated $IC_{50}$ (50% inhibition concentration), TGI (total growth inhibition) and $LC_{50}$ (50% lethal concentration) by nonlinear regression analysis was calculated (FIG. 2).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for reducing cellular proliferation comprising the step of exposing proliferative cells to an epithelial layer tissue powder extract derived from *Cucumaria frondosa* (*C. frondosa*) prepared by a method comprising a) generating an epithelial layer tissue powder from an epithelial layer of *C. frondosa*; b) extracting said powdered epithelial layer tissue powder with a mixture of isopropanol and water to generate a epithelial layer tissue powder extract; and c) preparing a treatment formulation comprising said epithelial layer tissue powder extract.

2. The method of claim 1, wherein said epithelial layer tissue powder extract is further prepared by step d) extracting said epithelial layer tissue powder extract with chloroform/methanol and retrieving at least a portion of a precipitate formed.

3. The method of claim 1, wherein said epithelial layer tissue powder extract is further prepared by step d) extracting said epithelial layer tissue powder extract with chloroform/methanol and discarding at least a portion of a precipitate formed.

4. The method of claim 1, wherein said cellular proliferation is associated with cancer.

5. The method of claim 1, wherein said cells are located in vivo in a subject.

6. The method of claim 3, wherein said cancer comprises pancreatic cancer.

7. The method of claim 3, wherein said subject is a human.

8. The method of claim 1, wherein said cells are further exposed to a second compound having anti-proliferative properties.

9. A therapeutic composition comprising an effective amount of an epithelial layer tissue powder extract derived from *C. frondosa* epithelial skin powder, wherein said epithelial layer tissue powder extract is prepared by the method comprising a) generating an epithelial layer tissue powder from an epithelial layer of *C. frondosa*; and b) extracting said powdered epithelial layer tissue powder with a mixture of isopropanol and water to generate a epithelial layer tissue powder extract.

10. The therapeutic composition of claim 9, wherein said epithelial layer tissue powder extract is further prepared by step c) extracting said epithelial layer tissue powder extract with chloroform/methanol and retrieving at least a portion of a precipitate formed.

11. The therapeutic composition of claim 9, wherein said epithelial layer tissue powder extract is further prepared by step c) extracting said epithelial layer tissue powder extract with chloroform/methanol and discarding at least a portion of a precipitate formed.

12. The composition of claim 9, wherein said composition further comprises a second anti-proliferative compound.

* * * * *

UNITED STATES PATENT AND TRADEMARK OFFICE
CERTIFICATE OF CORRECTION

| | |
|---|---|
| PATENT NO. | : 7,335,382 B1 |
| APPLICATION NO. | : 11/066802 |
| DATED | : February 26, 2008 |
| INVENTOR(S) | : Xian-Zhong Ding, Thomas E. Adrian and Peter D. Collin |

It is certified that error appears in the above-identified patent and that said Letters Patent is hereby corrected as shown below:

On the title page item 73: Add Co-Assignee "Coastside Bio Resources, Stonington, ME (US)" to already existing Assignee, Northwestern University.

Signed and Sealed this

Seventh Day of April, 2009

JOHN DOLL
*Acting Director of the United States Patent and Trademark Office*